US00PP34389P2

(12) United States Plant Patent
Beekenkamp

(10) Patent No.: US PP34,389 P2
(45) Date of Patent: Jun. 28, 2022

(54) ***BEGONIA* PLANT NAMED 'BKPBEWFBC'**

(50) Latin Name: *Begonia boliviensis*
Varietal Denomination: BKPBEWFBC

(71) Applicant: BEEKENKAMP PLANTS B.V., Maasdijk (NL)

(72) Inventor: Annie Cornelia Beekenkamp, Maasdijk (NL)

(73) Assignee: BEEKENKAMP PLANTS B.V., Maasdijk (NL)

( * ) Notice: Subject to any disclaimer, the term of this patent is extended or adjusted under 35 U.S.C. 154(b) by 39 days.

(21) Appl. No.: 17/339,900

(22) Filed: Jun. 4, 2021

(51) Int. Cl.
*A01H 5/02* (2018.01)
*A01H 6/18* (2018.01)

(52) U.S. Cl.
USPC ..... Plt./344
CPC ..... *A01H 6/185* (2018.05)

(58) Field of Classification Search
USPC ..... Plt./344
CPC ..... A01H 6/185
See application file for complete search history.

(56) References Cited

PUBLICATIONS

CPVO hit on a begonia plant named, 'BKPBEWFBC', QZ PBR 2021/1333, filed May 21, 2021, downloaded from url https://cpvo.europa.eu/en/applications-and-examinations/official-publications on Aug. 16, 2021.*

* cited by examiner

*Primary Examiner* — Anne Marie Grunberg
(74) *Attorney, Agent, or Firm* — C. Anne Whealy

(57) ABSTRACT

A new and distinct cultivar of *Begonia* plant named 'BKPBEWFBC', characterized by its compact, uniform, upright to outwardly spreading and semi-trailing plant habit; freely branching habit; dark green-colored leaves; freely flowering habit; and single-type female and male flowers that are pinkish red and white bi-colored.

2 Drawing Sheets

Figure 1:
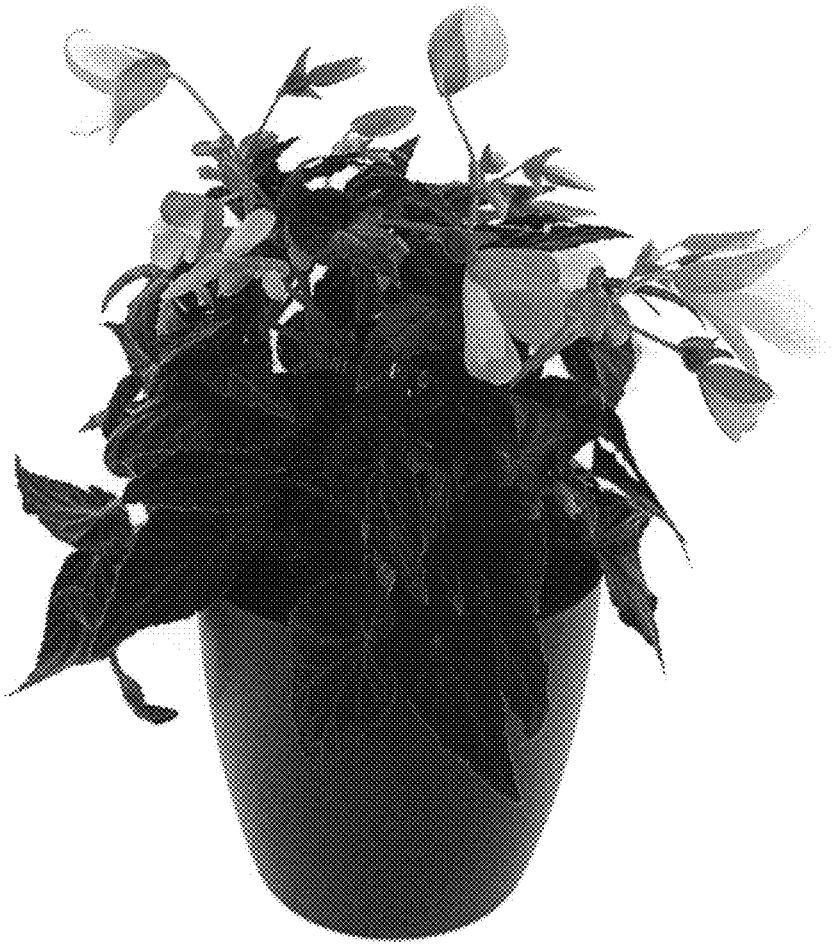

Botanical designation: *Begonia boliviensis*.
Cultivar denomination: 'BKPBEWFBC'.

STATEMENT REGARDING PRIOR DISCLOSURES BY THE INVENTOR & APPLICANT/ASSIGNEE

An European Community Plant Breeder's Rights application for the instant plant was filed by the Applicant/Assignee, Beekenkamp Plants B.V. of Maasdijk, The Netherlands on May 21, 2021, application number 2021/1333. Foreign priority is not claimed to this application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or the Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Begonia* plant, botanically known as *Begonia boliviensis*, and hereinafter referred to by the name 'BKPBEWFBC'.

The new *Begonia* plant is a product of a planned breeding program conducted by the Inventor in Maasdijk, The Netherlands. The objective of the breeding program is to create new uniform and freely branching *Begonia* plants with numerous attractive flowers and good garden performance.

The new *Begonia* plant originated from a cross-pollination in March, 2016 of a proprietary selection of *Begonia boliviensis* identified as code number H11-079-05, not patented, as the female, or seed, parent with a proprietary selection of *Begonia boliviensis* identified as code number 15-0000-05, not patented, as the male, or pollen, parent. The new *Begonia* plant was discovered and selected as a single flowering plant from within the progeny of the stated cross-pollination in a controlled greenhouse environment in Maasdijk, The Netherlands in September, 2016.

Asexual reproduction of the new *Begonia* plant by vegetative terminal cuttings in a controlled greenhouse environment in Maasdijk, The Netherlands, since December, 2016 has shown that the unique features of this new *Begonia* plant are stable and reproduced true to type in successive generations of asexual reproduction.

SUMMARY OF THE INVENTION

Plants of the new *Begonia* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'BKPBEWFBC'. These characteristics in combination distinguish 'BKPBEWFBC' as a new and distinct *Begonia* plant:

1. Compact, uniform, upright to outwardly spreading and semi-trailing plant habit.
2. Freely branching habit.
3. Dark green-colored leaves.
4. Freely flowering habit.
5. Single-type female and male flowers that are pinkish red and white bi-colored.

Plants of the new *Begonia* can be compared to plants of the female parent selection. Plants of the new *Begonia* differ primarily from plants of the female parent selection in the following characteristics:

1. Plants of the new *Begonia* are more upright than and not as trailing as plants of the female parent selection.
2. Flower tepals of plants of the new *Begonia* are pinkish red and white bi-colored whereas flower tepals of plants of the female parent selection are salmon and white bi-colored.

Plants of the new *Begonia* can be compared to plants of the male parent selection. Plants of the new *Begonia* differ primarily from plants of the male parent selection in the following characteristics:

1. Plants of the new *Begonia* are more upright than and not as trailing as plants of the male parent selection.
2. Flower tepals of plants of the new *Begonia* are pinkish red and white bi-colored whereas flower tepals of plants of the male parent selection are salmon and white bi-colored.

Plants of the new *Begonia* can be compared to plants of the *Begonia boliviensis* 'BKPBEWFER', disclosed in U.S. Plant Pat. No. 24,959. In side-by-side comparisons, plants of the new *Begonia* differ from plants of 'BKPBEWFER' in the following characteristics:

1. Plants of the new *Begonia* are more compact than and not as trailing as plants of 'BKPBEWFER'.
2. Flower tepals of plants of the new *Begonia* are pinkish red and white bi-colored whereas flower tepals of plants of 'BKPBEWFER' are bright red in color.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph on the first sheet (FIG. 1) is a side perspective view of a typical flowering plant of 'BKPBEWFBC' grown in a container.

Figure 2:
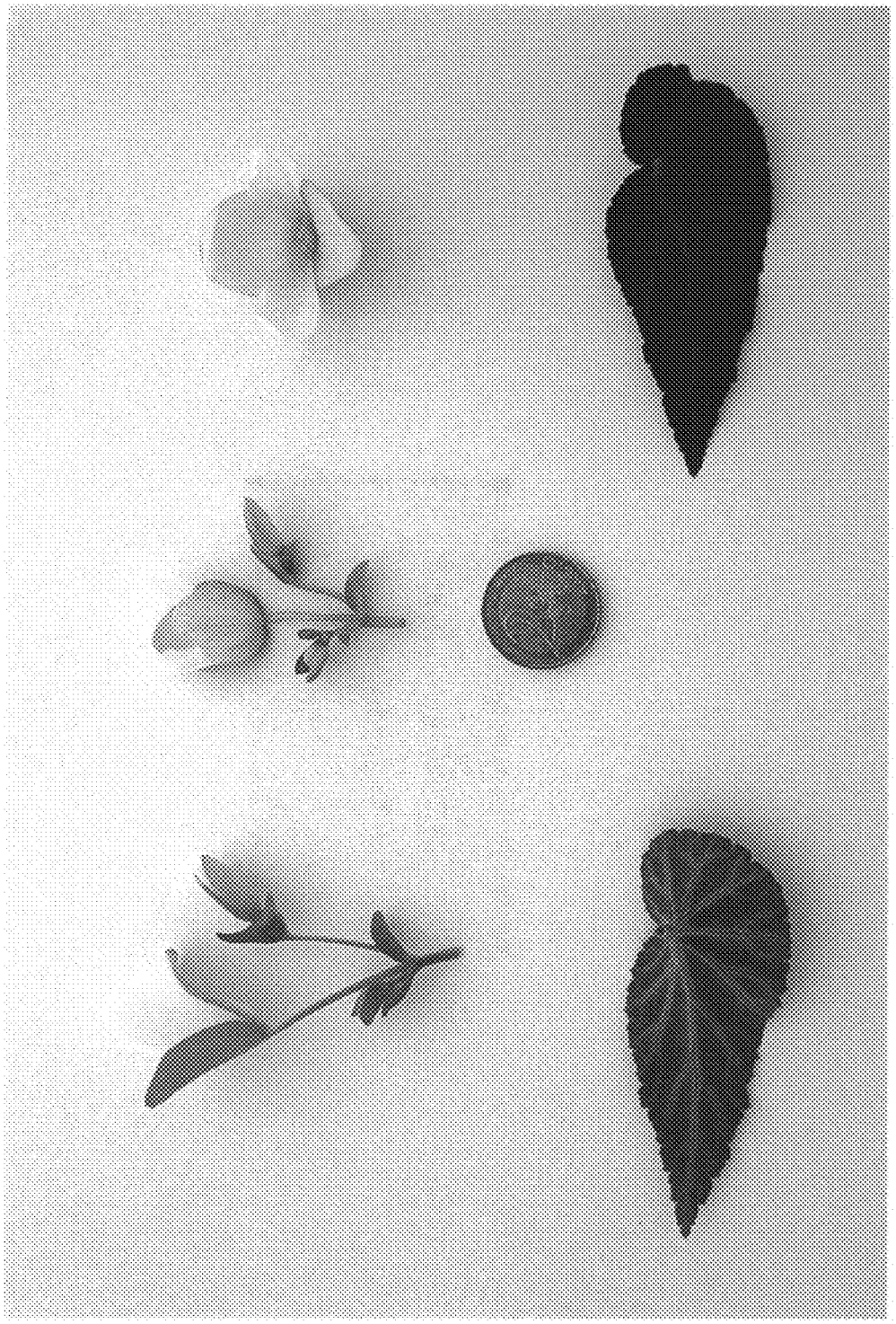

The photograph on the second sheet (FIG. 2) are close-up views of the upper and lower surfaces of typical leaves and developing and developed flowers of 'BKPBEWFBC'.

DETAILED BOTANICAL DESCRIPTION

Plants used for the aforementioned photographs and following observations and measurements were grown during the spring in 11-cm containers in a glass-covered greenhouse in Maasdijk, The Netherlands. During the production of the plants, day temperatures ranged from 19° to 20° C., night temperatures ranged from 18° C. to 19° C. and light levels averaged 6,000 lux. Plants were eleven weeks from planting rooted cuttings when the photographs and the description were taken. In the following description, color references are made to The Royal Horticultural Society Colour Chart, 2015 Edition, except where general terms of ordinary dictionary significance are used.

Botanical classification: *Begonia boliviensis* 'BKPBEWFBC'.

Parentage:

*Female, or seed, parent.*—Proprietary selection of *Begonia boliviensis* identified as code number H11-079-05, not patented.

*Male, or pollen, parent.*—Proprietary selection of *Begonia boliviensis* identified as code number 15-0000-05, not patented.

Propagation:

*Type.*—By vegetative tip cuttings.

*Time to initiate roots, summer and winter.*—About one week at temperatures ranging from 20° C. to 25° C.

*Time to produce a rooted young plant, summer.*—About 32 days at temperatures ranging from 20° C. to 25° C.

*Time to produce a rooted young plant, winter.*—About 35 days at temperatures ranging from 20° C. to 25° C.

*Root description.*—Fine, fibrous; typically beige in color, actual color of the roots is dependent on substrate composition, water quality, fertilizer type and formulation, substrate temperature and physiological age of roots; to date, plants of the new *Begonia* have not been observed to form tubers.

*Rooting habit.*—Freely branching; dense.

Plant description:

*Plant and growth habit.*—Compact, uniform, upright to outwardly spreading and semi-trailing plant habit; plant shape roughly globular; freely branching habit with about four basal branches each with about five lateral branches developing per plant; moderately vigorous growth habit and moderate growth rate.

*Plant height, soil level to top of foliar plane.*—About 15.6 cm.

*Plant height, soil level to top of floral plane.*—About 18.5 cm.

*Plant width.*—About 26.3 cm.

*Lateral branch description.*—Length: About 7.4 cm. Diameter: About 4 mm. Internode length: About 2.1 cm. Strength: Moderately weak, bending with the weight of the leaves and flowers. Aspect: About 30° from vertical. Texture and luster: Smooth, glabrous; slightly glossy. Color, developing: Close to 152A slightly tinged with close to 182B. Color, developed: Darker than a blend of 148A and 197A; at the internodes, close to 144A.

*Leaf description.*—Arrangement: Alternate, distichous; simple. Length: About 8.1 cm. Width: About 3.5 cm. Shape: Lanceolate. Apex: Acute. Base: Oblique; lobes not imbricate. Margin: Crenate; teeth apices, abruptly acute. Texture and luster, upper and lower surfaces: Sparsely pubescent; not rugose; slightly velvety; slightly glossy. Venation pattern: Pinnate. Color: Developing leaves, upper surface: Close to 147A tinged with close to 200B. Developing leaves, lower surface: Close to 183A to 183B. Fully expanded leaves, upper surface: Darker than a blend of close to 147A and N189A; venation, close to 136C. Fully expanded leaves, lower surface: Close to 183A; venation, close to 146A to 146B. Petioles: Length: About 4.5 cm. Diameter: About 2.5 mm.

Texture and luster, upper and lower surfaces: Sparsely pubescent; moderately glossy. Strength: Low. Color, upper surface: Close to 152A, slightly tinged with close to 176A, mostly at the leaf attachment. Color, lower surface: Close to 152A, slightly tinged with close to 176A. Stipules: Quantity per leaf: Two at the base of each leaf. Length: About 7 mm. Width: About 3.5 mm. Shape: Ovate. Apex: Obtuse. Base: Broadly cuneate. Margins: Entire, finely ciliate. Color, upper and lower surfaces: Close to 145C; venation, close to 183C.

Flower description:

*Flowering habit*.—Rotate female and male flowers are single-types; flowers arranged in simple axillary cymes; freely flowering habit with about four flowers per cyme and about 80 flowers developing per plant during the flowering season; flowers face outwardly to slightly nodding or drooping.

*Fragrance*.—None detected.

*Natural flowering season*.—Long flowering period; plants flower freely and continuously from spring into the autumn in The Netherlands.

*Flower longevity*.—Individual flowers last about ten days on the plant; flowers not persistent.

*Inflorescence height* (*including peduncle*).—About 13 cm.

*Inflorescence diameter*.—About 8 cm.

*Flower buds, female flowers*.—Length: About 2.3 cm. Diameter, flattened: About 1 cm to 1.4 cm. Shape: Oblong; flattened. Texture and luster: Smooth, glabrous; velvety; matte. Color, upper surface: Close to 37B to 37C. Color, lower surface: Close to 145D; developing ovary, close to 144C.

*Flower buds, male flowers*.—Length: About 1.8 cm. Diameter, flattened: About 6 mm to 14 mm. Shape: Roughly ovate; flattened. Texture and luster: Smooth, glabrous; velvety; matte. Color, upper surface: Close to 44D to slightly lighter than 44D. Color, lower surface: Close to a blend of 145D and 150D.

*Female flowers*.—Size: About 4.2 cm by 4.3 cm. Depth: About 3.4 cm. Tepals: Quantity per flower and arrangement: Five in two whorls; inner whorl with three tepals and outer whorl with two tepals. Length, inner tepals: About 3 cm. Length, outer tepals: About 2.8 cm. Width, inner tepals: About 1.4 cm. Width, outer tepals: About 1.5 cm. Shape, inner tepals: Narrowly oblong to narrowly obovate. Shape, outer tepals: Ovate to obovate. Apex, inner tepals: Obtuse. Apex, outer tepals: Obtuse to broadly and bluntly acute. Base, inner and outer tepals: Cuneate. Margin, inner and outer tepals: Entire; not undulate. Texture and luster, inner and outer tepals, upper surface: Smooth, glabrous; moderately velvety; matte. Texture and luster, inner and outer tepals, lower surface: Smooth, glabrous; slightly velvety; slightly glossy. Color, inner tepals: When opening, upper surface: Close to 157A. When opening, lower surface: Close to 157A tinged with close to 44D to lighter than 44D. Fully opened, upper surface: Close to 157D; venation, close to 195B; color does not change with subsequent development. Fully opened, lower surface: Close to 157D flushed with close to 38A and 38B; venation, close to 195D; color does not change with subsequent development. Color, outer tepals: When opening, upper surface: Close to 157A. When opening, lower surface: Close to 44D. Fully opened, upper surface: Close to 36A; venation, close to 35C; color does not change with subsequent development. Fully opened, lower surface: Close to 41B; venation, close to 195D; color does not change with subsequent development. Tepaloids: None observed on female flowers.

*Male flowers*.—Size: About 6 cm by 6 cm. Depth: About 2.4 cm. Tepals: Quantity per flower and arrangement: Four in two whorls; inner whorl with two tepals and outer whorl with two tepals. Length, inner tepals: About 3.8 cm. Length, outer tepals: About 3.4 cm. Width, inner tepals: About 1.5 cm. Width, outer tepals: About 2.3 cm. Shape, inner tepals: Narrowly oblong to oblanceolate. Shape, outer tepals: Ovate. Apex, inner and outer tepals: Obtuse. Base, inner and outer tepals: Cuneate. Margin, inner and outer tepals: Entire; not undulate. Texture and luster, inner and outer tepals, upper surface: Smooth, glabrous; moderately velvety; matte. Texture and luster, inner and outer tepals, lower surface: Smooth, glabrous; slightly velvety; slightly glossy. Color, inner tepals: When opening, upper surface: Close to 157B. When opening, lower surface: Close to 157A tinged with close to 44D to lighter than 44D. Fully opened, upper and lower surfaces: Close to 157D, towards the base, close to 36C; venation, close to 195D; color does not change with subsequent development. Color, outer tepals: When opening, upper surface: Close to 157B tinged with close to 35D. When opening, lower surface: Close to 41C flushed with close to 157A. Fully opened, upper surface: Close to 36A to 36D; venation, close to 195D; color does not change with subsequent development. Fully opened, lower surface: Close to 41B, occasionally, variably and strongly tinged and flushed with close to 38A to 38D to lighter than 38D; venation, close to 195D; color does not change with subsequent development. Tepaloids: None observed on male flowers.

*Peduncles*.—Length: About 7.7 cm. Diameter: About 3 mm. Angle: About 45° from lateral branch axis. Strength: Moderately weak; flexible and bending with the weight of the flowers. Texture and luster: Smooth, glabrous; moderately glossy. Color, upper and lower surfaces: Close to 146D, tinged with close to 172B, mostly towards the pedicel attachment.

*Pedicels, female flowers*.—Length: About 4.3 cm. Diameter: About 1.75 mm. Angle: About 45° from the peduncle axis. Strength: Moderately weak; flexible, bending with the weight of the flowers. Texture and luster: Smooth, glabrous; glossy. Color, upper surface: Close to a blend of 45A and 185A. Color, lower surface: Close to 177D.

*Pedicels, male flowers*.—Length: About 3.5 cm. Diameter: About 1.75 mm. Angle: Mostly upright. Strength: Moderately weak; flexible, bending with the weight of the flowers. Texture and luster: Smooth, glabrous; glossy. Color, upper surface: Close to 34B. Color, lower surface: Close to 173D.

*Flower bracts*.—Quantity per flower and arrangement: Two, at the top of the peduncles. Length: About 1.2 cm. Width: About 1 cm. Shape: Broadly obovate. Apex: Rounded. Base: Broadly cuneate. Margin:

Entire; ciliate. Texture and luster, upper and lower surfaces: Smooth, glabrous; slightly glossy. Color, upper and lower surfaces: Close to 173A to 173B.

*Reproductive organs*.—Androecium: Present only on male flowers. Stamen quantity per flower: About 30. Filament length: About 3.5 mm. Filament color: Close to 13C. Anther size: About 1 mm by 1.5 mm. Anther shape: Obovate. Anther color: Close to 5B. Amount of pollen: Scarce. Pollen color: Close to 4D. Gynoecium: Present only on female flowers. Quantity per flower: About three. Pistil length: About 6 mm. Stigma diameter: About 4 mm. Stigma shape: Cleft. Stigma color: Close to 9A. Style length: About 5 mm. Style color: Close to 9A. Ovary color: Close to 144B to 144C, at the apex, close to 42B. Seeds and fruits: To date, seed and fruit development have not been observed on plants of the new *Begonia*.

Pathogen & pest resistance: To date, resistance to pathogens and pests common to *Begonia* plants has not been observed on plants of the new *Begonia*.

Temperature tolerance: Plants of the new *Begonia* have been observed to tolerate high temperatures of about 35° C. and to be suitable for USDA Hardiness Zones 10 to 12.

It is claimed:

1. A new and distinct *Begonia* plant named 'BKPBE-WFBC' as illustrated and described.

* * * * *